United States Patent [19]
Gadient

[11] 3,946,036
[45] Mar. 23, 1976

[54] 6,11-DIHYDRO-11-OXO-DIBENZO[B,E]THIEPINE-2-ACETIC ACIDS

[75] Inventor: Fulvio Gadient, Birsfelden, Switzerland

[73] Assignee: Sandoz Ltd., Basel, Switzerland

[22] Filed: Sept. 9, 1974

[21] Appl. No.: 504,428

[30]     Foreign Application Priority Data
Sept. 13, 1973   Switzerland..................... 13178/73
Sept. 13, 1973   Switzerland..................... 13179/73
May 9, 1974      Switzerland..................... 6366/74

[52] U.S. Cl. ............................ 260/327 B; 424/275
[51] Int. Cl.² ........................................ C07D 337/12
[58] Field of Search ............................. 260/327 B

[56]             References Cited
             UNITED STATES PATENTS
3,725,409    4/1973   Protiva et al. ................. 260/268 TR
        FOREIGN PATENTS OR APPLICATIONS
47-00425     1/1972   Japan ............................ 260/327 B

*Primary Examiner*—Randolph, John D.
*Assistant Examiner*—C. M. S. Jaisle
*Attorney, Agent, or Firm*—Gerald D. Sharkin; Robert S. Honor; Thomas O. McGovern

[57]              ABSTRACT

The present invention provides compounds of formula I,

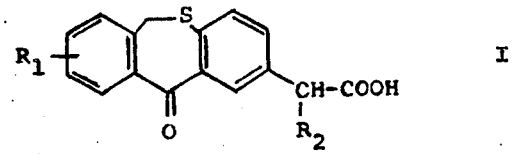

wherein
  $R_1$ is hydrogen, fluorine, chlorine, bromine, hydroxyl, lower alkyl, lower alkoxy, amino or lower acylamino, and
  $R_2$ is hydrogen or lower alkyl,
useful as antiphlogistic and anti-arthritic agents.

6 Claims, No Drawings

6,11-DIHYDRO-11-OXO-DIBENZO[B,E]THIEPINE-2-ACETIC ACIDS

The present invention relates to heterocyclic compounds.

In accordance with the invention there are provided compounds of formula I,

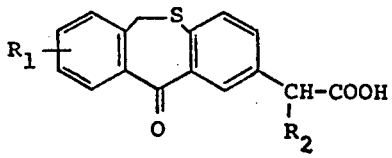

wherein
R₁ is hydrogen, halogen of atomic number from 9 to 35, hydroxyl, lower alkyl, lower alkoxy, amino or lower acylamino, and
R₂ is hydrogen or lower alkyl.

Further, in accordance with the invention a compound of formula I may be obtained by a process comprising
a. converting a compound of formula II,

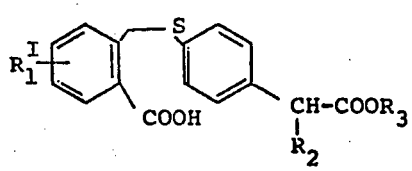

wherein
$R_1{}'$ is hydrogen, halogen of atomic number from 9 to 35, lower alkyl, lower alkoxy or lower acylamino,
R₂ is as defined above, and
R₃ is hydrogen or lower alkyl,
or a reactive acid derivative thereof, into a compound of formula Ia,

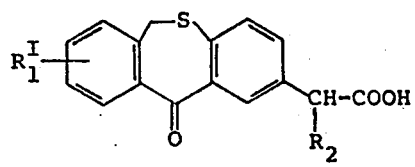

wherein $R_1{}'$ and R₂ are as defined above,
or
b. hydrolyzing a compound of formula III,

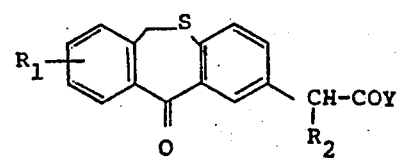

wherein
R₁ and R₂ are as defined above, and
Y is a leaving group, or
c. converting a compound of formula Ib,

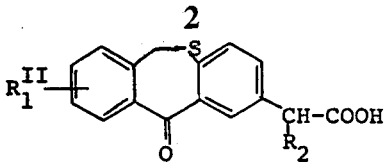

wherein
$R_1{}''$ is acylamino and
R₂ is as defined above,
into a compound of formula Ic,

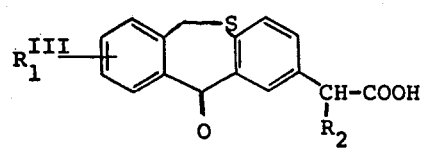

wherein
$R_1{}'''$ is amino and
R₂ is as defined above, or
d. converting a compound of formula Ic into a compound of formula Id,

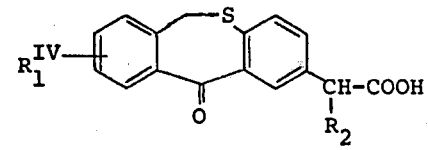

wherein
$R_1{}^{IV}$ is hydroxy and
R₂ is as defined above.

R₁ in the compounds of formula I preferably signifies hydrogen or chlorine. Any substituent R₁ is preferably present in the 8- or 9-position of the ring structure. When R₁ is lower alkyl or lower alkoxy, these groups preferably contain 1 to 3 carbon atoms and especially signify methyl or methoxy. When R₁ is acylamino, this preferably contains 2 to 5 carbon atoms and especially signifies acetamino. When the substituent R₂ is lower alkyl, this preferably contains 1 to 3 carbon atoms. R₂ preferably signifies methyl or hydrogen. Any carbon-containing radical not particularly defined herein preferably has up to 5 carbon atoms.

The cyclization of a compound of formula II in accordance with process (a) is preferably effected in the presence of a strongly acid condensation agent. The reaction is conveniently effected in an inert organic solvent, e.g. an aromatic solvent such as benzene, toluene or nitrobenzene, or a chlorinated hydrocarbon such as methylene chloride or dichloroethane. Examples of suitable acid condensation agents are: strong acids, preferably polyphosphoric acid or methanesulphonic acid/phosphorus pentoxide, for example a mixture of about 10% of phosphorus pentoxide in methanesulphonic acid. The reaction temperature preferably is between about 70° and 160°C. In place of an acid of formula II, a reactive derivative of such an acid may alternatively be used for the cyclization. Examples of suitable reactive derivatives of an acid of formula II are the acid halides or mixed anhydrides of an acid of formula II and a lower organic carboxylic acid or, alternatively, a lower alkyl ester of an acid of formula II. In accordance with a process variant, an acid of formula II, wherein $R_3$ is lower alkyl, may, for example, be first converted into a reactive acid derivative, of at least the 2-carboxy-phenyl moiety, e.g. an acid chloride thereof with an organic acid chloride, e.g. thionyl chloride, and this acid chloride may subsequently be cyclized under the reaction conditions of a Friedel-Crafts reaction in the presence of a Friedel-Crafts catalyst, e.g. aluminium chloride or tin tetrachloride, e.g. in an inert organic solvent. Examples of suitable solvents for the Friedel-Crafts reaction are: nitrobenzene, carbon disulphide or chlorinated hydrocarbons such as methylene chloride and tetrachloroethane. The reaction conditions for the hydrolysis of the organometallic complex, formed as intermediary during the Friedel-Crafts reaction, are chosen such that the acetic acid lower alkyl ester group may be hydrolyzed simultaneously.

Process variant (b) may be effected under conventional hydrolysis conditions bearing in mind the nature of Y and $R_1$. Y may be chlorine or —$OR_4$ wherein $R_4$ is lower alkyl. For example, a compound of formula III may be allowed to react with water. A suitable temperature may be between room temperature and about 100°C. The reaction is conveniently effected in the presence of a base, e.g. an alkali metal or alkaline earth metal hydroxide, or in the presence of an acid catalyst, e.g. a mineral acid such as hydrochloric or sulphuric acid, or an organic sulphonic acid. The hydrolysis is however preferably effected in an alkaline medium, e.g. with at least an equivalent amount of an aqueous alkali metal hydroxide solution, e.g. at room temperature or at a slightly elevated temperature. Examples of suitable inert water miscible organic solvents which may be present are: lower alcohols such as methanol or ethanol, acetone, tetrahydrofuran or dioxane.

Process variant (c) may be effected in conventional manner for the conversion of an acylamino group into an amino group in analogous compounds. The reaction is conveniently effected in a concentrated aqueous acid medium, e.g. aqueous concentrated hydrochloric acid. Suitable reaction temperatures may be between 100° and 120°C.

Process variant (d) may be effected in conventional manner for the conversion of a phenylamine into a phenol in analogous compounds. The amine may be diazotized in conventional manner followed by hydrolysis of the diazonium salt in conventional manner.

The resulting compounds of formula I may be isolated from the reaction mixture and purified in known manner. If desired, the free acid forms may be converted into salt forms thereof and vice versa. A suitable salt is the sodium salt.

The starting materials may, for example, be produced as follows:

a'. A compound of formula III may, for example, be obtained by cyclizing a compound of formula IIa,

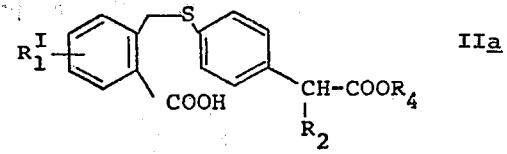

wherein $R_1{}'$, $R_2$ and $R_4$ are as defined above, and, if desired, converting the acylamino group into the amino group in any resulting compound of formula IIIc, $$R_1^{II}\text{—} \underset{O}{\text{[dibenzothiepinone]}} \text{—CH}(R_2)\text{—COOR}_4 \quad \text{IIIc}$$

wherein
$R_1{}^{II}$ is acylamino, and
$R_2$ and $R_4$ are as defined above,
and, if desired, diazotizing the amino group and converting it into the hydroxy group by hydrolysis, and, if desired, etherifying the hydroxy group. The reaction conditions for the cyclization reaction should be chosen such that an ester hydrolysis is avoided. For example, a compound of formula IIa may first be converted into an acid chloride thereof and this may subsequently be subjected to a Friedel-Crafts cyclization. The reaction may be effected under the reaction conditions described in process variant (a). The decomposition of the organometallic complex, formed as intermediary during the Friedel-Crafts reaction, must be effected under such mild reaction conditions, for example low temperatures, preferably between 0° and room temperature, that a hydrolysis of the ester group is avoided. An ester of formula III may alternatively be obtained by esterifying a corresponding acid with a lower alcohol $R_4$—OH in known manner. The conversion of the acylamino group into an amino group may be effected in known manner, e.g. by hydrolysis in a strongly acid medium at an elevated temperature, e.g. in approx. 10 N hydrochloric acid at a temperature between 100° and 120° C, whereby the ester group is naturally likewise split, so that the corresponding acid is obtained, which may optionally be again esterified in known manner. The diazotization of the amino compound and the subsequent boiling of the diazonium salt to obtain the hydroxy compound are effected in accordance with known methods and the resulting crude hydroxy acid may again be esterified in known manner. Any etherification of the hydroxy group may be effected using known etherification methods.

b'. A compound of formula IIIa, $$R_1^I \text{—}\underset{O}{\underset{\|}{\text{[thioxanthone ring]}}}\text{—}\underset{R_2^I}{\underset{|}{CH}}\text{—}COOR_4 \quad \text{IIIa}$$

wherein
$R_1^I$ and $R_4$ are as defined above, and
$R_2^I$ is lower alkyl,
may, for example, be obtained by alkylating a compound of formula IIIb, $$R_1^I \text{—}\underset{O}{\underset{\|}{\text{[thioxanthone ring]}}}\text{—}CH_2\text{—}COOR_4 \quad \text{IIIb}$$

wherein $R_1^I$ and $R_4$ are as defined above,
by reaction with a compound of formula IV, $$R_2^I\text{—}X \quad \text{IV}$$

wherein
$R_2^I$ is as defined above, and
X is the acid radical of a reactive ester.

The alkylation may be effected in known manner in an inert organic solvent, preferably an aprotic, polar solvent, e.g. dimethyl formamide, dimethyl sulphoxide, hexamethylphosphoric acid triamide, or an ether such as dimethoxyethane or tetrahydrofuran, or a mixture of these esters and liquid ammonia or, alternatively, in an aromatic hydrocarbon such as benzene or toluene, e.g. in the presence of a strongly basic condensation agent, capable of forming the anion of the compound of formula IIIb. It is preferred to use a compound of formula IV wherein X is halogen or a mesyloxy or tosyloxy group. Examples of suitable basic condensation agents are: alkali metals, alkali metal amides such as sodium amide, diisopropyl-lithium amide, alkali metal hydrides such as sodium hydride or alkali metal alcoholates. The reaction may, for example, be effected at a temperature between about −50° and about +60°C.

c'. A compound of formula IIb, $$R_1^I\text{—}\underset{COOH}{\text{[diaryl-S ring]}}\text{—}\underset{R_2}{\underset{|}{CH}}\text{—}COOH \quad \text{IIb}$$

wherein $R_1^I$ and $R_2$ are as defined above,
may, for example, be obtained by hydrolysis of a compound of formula IIa or an ester thereof.

d'. A compound of formula IIc, $$R_1^I\text{—}\underset{COOR_5}{\text{[diaryl-S ring]}}\text{—}\underset{R_2^I}{\underset{|}{CH}}\text{—}COOR_4 \quad \text{IIc}$$

wherein
$R_1^I$, $R_2^I$ and $R_4$ are as defined above, and
$R_5$ is lower alkyl,
may, for example, be obtained by alkylating a compound of formula IId, $$R_1^I\text{—}\underset{COOR_5}{\text{[diaryl-S ring]}}\text{—}CH_2\text{—}COOR_4 \quad \text{IId}$$

wherein $R_1^I$, $R_4$ and $R_5$ are as defined above, by reaction with a compound of formula IV. The alkylation may be effected in the presence of a strongly basic condensation agent under the reaction conditions described in process (b').

e'. A compound of formula IIe, $$R_1^I\text{—}\underset{COOR_6}{\text{[diaryl-S ring]}}\text{—}\underset{R_2}{\underset{|}{CH}}\text{—}COOR_4 \quad \text{IIe}$$

wherein
$R_1^I$, $R_2$ and $R_4$ are as defined above, and
$R_6$ is hydrogen or lower alkyl,
may, for example, be obtained by reacting a compound of formula V, $$HS\text{—}\underset{}{\text{[phenyl]}}\text{—}\underset{R_2}{\underset{|}{CH}}\text{—}COOR_4 \quad \text{V}$$

wherein $R_2$ and $R_4$ are as defined above,
with a compound of formula VIa, $$R_1^I\text{—}\underset{O}{\underset{\|}{\text{[phthalide ring]}}} \quad \text{VIa}$$

wherein $R_1^I$ is as defined above,
or with a compound of formula VIb $$R_1^I\text{—}\underset{COOR_5}{\text{[phenyl]}}\text{—}CH_2\text{—}Y \quad \text{VIb}$$

wherein
$R_1^I$ and $R_5$ are as defined above, and
Y is chlorine or bromine.

The reaction is preferably effected in the presence of a basic condensation agent, preferably an alkali metal alcoholate, at a temperature between preferably about 80° and 150° C.

f'. A compound of formula V may, for example, be obtained by forming the diazonium salt in the usual manner from a 2-(4-aminophenyl)carboxylic acid of formula VII,

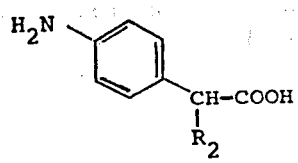

wherein $R_2$ is as defined above,
reacting the diazonium salt with an alkali xanthogenate and subsequently working up in known manner to obtain a 2-(4-mercaptophenyl)carboxylic acid and esterifying this in accordance with known methods.

g'. A compound of formula VIb may, for example, be obtained by brominating or chlorinating in known manner an o-toluic acid derivative of formula VIII, $$R_1^I \underset{COOR_5}{\overset{CH_3}{\bigodot}} \qquad VIII$$

wherein $R_1'$ and $R_5$ are as defined above, or an alcohol of formula IX, $$R_1^I \underset{COOR_5}{\overset{CH_2OH}{\bigodot}} \qquad IX$$

wherein $R_1'$ and $R_5$ are as defined above.

Insofar, as the production of the starting materials is not described, these are known or may be produced in accordance with known processes or in a manner analogous to the processes described herein or to known processes.

In the following non-limitative Examples all temperatures are indicated in degrees Centigrade.

EXAMPLE 1

6,11-dihydro-11-oxo-dibenzo[b,e]thiepine-2-acetic acid [process variant (a)]

7 G of 4-(2-carboxy-benzyl-thio)phenylacetic acid are added to 70 g of polyphosphoric acid heated to 130°, and the mixture is heated at the same temperature, while stirring, for 10 minutes. The reaction mixture is subsequently poured on ice water and the aqueous phase is extracted with ethyl acetate. After washing with water and drying over magnesium sulphate, the solvent is removed by distillation, whereby the title compound is obtained as crystalline residue. After recrystallization from ethyl acetate/ether, the title compound has a M.P. of 164°–166°.

The starting material may, for example, be produced as follows:

a. 4-mercapto-phenyl-acetic acid

A solution of 27.6 g of sodium nitrite in 200 cc of water is added dropwise at 0°, while stirring, to a suspension of 60.4 g of 4-aminophenyl-acetic acid in 200 cc of water and 80 cc of concentrated hydrochloric acid. After the addition is complete, the reaction mixture is stirred at the same temperature for a further 45 minutes. This cold diazonium salt solution is then added dropwise at room temperature to a mixture of 74 g of potassiumethyl xanthogenate, 120 cc of water and 300 cc of a 2 N soda solution, and heating is effected to 45° until gas evolution stops. The mixture is subsequently cooled to room temperature, the pH is adjusted to 1 with concentrated hydrochloric acid and the oiled xanthogenate ester is extracted with ether. After removing the solvent by distillation, the ester is taken up in 500 cc of ethanol, a solution of 90 g of potassium hydroxide in 500 cc of water is added and boiling at reflux is effected for 20 hours. The major portion of the ethanol is subsquently removed by the distillation at reduced pressure, the aqueous phase is cooled with ice, rendered acid with concentrated hydrochloric acid while stirring well, and extracted with ether. The ether extract is dried over sodium sulphate, the solvent is removed by distillation, whereby 4-mercapto-phenylacetic acid crystallizes. After recrystallization from ether/pentane, the acid has a M.P. of 101° to 103°.

b. 4-mercapto-phenyl-acetic acid ethyl ester 70 g G 4-mercapto-phenyl-acetic acid are heated at reflux for 30 minutes in 500 cc of 4 N hydrochloric acid in ethanol. The reaction mixture is then completely concentrated at reduced pressure. The oily residue is divided between ether and water, the ether phase is subsequently washed with a 10% sodium bicarbonate solution and water, is dried over sodium sulphate, and the solvent is removed by distillation. The crude 4-mercapto-phenyl-acetic acid ethyl ester, obtained as oily residue, may be purified by distillation; B.P. 103° at 0.4 mm of Hg.

c. 4-(2-carboxy-benzyl-thio)phenyl-acetic acid ethyl ester 19.6 G of 4-mercapto-phenyl-acetic acid ethyl ester and 13.4 g of phthalide are added to a sodium ethylate solution produced from 2.3 g of sodium and 55 cc of ethanol, and the mixture is heated in an oil bath of 110° for 20 hours. The reaction solution is subsequently concentrated at reduced pressure, the crystalline residue is dissolved in water, cooled with ice and acidified with 5 N hydrochloric acid. The aqueous phase is extracted with ether, the ether extract is washed with water, dried over sodium sulphate, purified with animal charcoal, and the solvent is completely concentrated. 4-(2-carboxy-benzyl-thio)phenylacetic acid ethyl ester is obtained as crystalline residue which is recrystallized from ether/pentane (M.P. 93° to 94°).

d. A solution of 4.75 g of potassium hydroxide in 20 cc of water is added to 7 g of 4-(2-carboxybenzyl-thio)-phenyl-acetic acid ethyl ester in 50 cc of ethanol, and the mixture is stirred at room temperature for 20 hours. The solution is then concentrated at reduced pressure, the residue is taken up in water and extracted with ether. The aqueous phase is subsequently acidified with 5 N hydrochloric acid and extracted with ethyl acetate. After washing the ethyl acetate extract with water and drying over sodium sulphate, the solvent is removed by distillation, whereby 4-(2-carboxy-benzyl-thio)phenyl-acetic acid is obtained as crystalline residue. M.P. 169° (from ethyl acetate/pentane).

EXAMPLE 2

6,11-dihydro-11-oxo-dibenzo[b,e]thiepine-2-acetic acid

5 G of 4-(2-carboxy-benzyl-thio)phenylacetic acid ethyl ester are added to 30 g of polyphosphoric acid heated to 120° and the mixture is heated at the same temperature for 2 hours. The reaction mixture is subsequently poured on ice water, the aqueous phase is extracted with ethyl acetate and the insoluble portions are filtered off. After washing with water and drying over magnesium sulphate, the solvent is removed by distillation. The residue, containing the title compound, is recrystallized from ethyl acetate/ether; M.P. 164°–166°.

EXAMPLE 3

6,11-dihydro-11-oxo-dibenzo[b,e]thiepine-2-acetic acid 7.0 G of 4-(2-chloro-carbonyl-benzyl-thio)phenyl-acetic acid ethyl ester are dissolved in 30 cc of nitrobenzene and this solution is added dropwise at room temperature to a solution of 3.32 g of aluminium chloride in 50 cc of nitrobenzene. The resulting red solution is heated in an oil bath of 100° for 3 hours. The oil bath is then removed, decomposition is effected with 20 g of ice and the two-phase mixture containing crude 6,11-dihydro-11-oxo-dibenzo[b,e]thiepine-2-acetic acid ethyl ester is again stirred at 100° for 2 hours with the addition of 20cc of 10 N hydrochloric acid. The reaction mixture is subsequently cooled, diluted with ether, the organic phase is separated, washed with water and extracted with a 10% sodium bicarbonate solution. The alkaline extract is washed with ether, acidified with 5 N hydrochloric acid and again extracted with ether. The organic extract is washed with water, dried with sodium sulphate, purified with charcoal, filtered and concentrated at reduced pressure. The resulting title compound crystallizes from ether, M.P. 162°–164°.

The starting material may be obtained as follows:
a. 66 cc of thionyl chloride are added at room temperature to 13.2 g of 4-(2-carboxy-benzyl-thio)phenyl-acetic acid ethyl ester and the mixture is stirred for 90 minutes until gas evolution stops. The mixture is completely concentrated by evaporation at reduced pressure and the resulting light yellow oil is dissolved in ether, whereby 4-(2-chloro-carbonyl-benzyl-thio)-phenyl-acetic acid ethyl ester precipitates in the form of light yellow crystals. M.P. 78°–79°.

EXAMPLE 4

6,11-dihydro-11-oxo-dibenzo[b,e]thiepine-2-acetic acid 5.0 G of 4-(2-chloro-carbonyl-benzyl-thio)phenyl-acetyl chloride are added to 50 g of polyphosphoric acid and heated in an oil bath of 100°. An initial separation of hydrochloric acid comes to an end rapidly, after 75 minutes the reaction is complete producing crude 6,11-dihydro-11-oxo-dibenzo[b,e]thiepine-2-acetyl chloride. Working up is effected by pouring the dark brown solution on 200 cc of hot water (80°) and stirring for 10 minutes. White or light beige crystals precipitate and are extracted with ethyl acetate. The organic phase is separated, washed with water, dried with sodium sulphate, purified with charcoal, filtered, and the solvent is removed by distillation at reduced pressure. The residue is dissolved in ether, whereby the title compound is obtained in crystalline form. M.P. 162°–164°.

The starting material may be obtained as follows:
a. 70 Cc of thionyl chloride are added to 7.0 g of 4-(2-carboxy-benzyl-thio)phenyl-acetic acid and boiled in a water bath of 90° for 45 minutes until gas evolution stops. The mixture is completely concentrated by evaporation at reduced pressure and the 4-(2-chloro-carbonyl-benzyl-thio)phenyl-acetyl chloride, obtained as light yellow oil, is crystallized from ether. M.P. 62°–64°.

EXAMPLE 5

9-chloro-6,11-dihydro-11-oxo-dibenzo[b,e]thiepine-2-acetic acid

The title compound is obtained in a manner analogous to that described in Example 1 or 2, using 4-(2-carboxy-4-chloro-benzyl-thio)phenyl-acetic acid or the ethyl ester thereof as starting material. M.P. 187°–189° (from ethyl acetate/pentane).

The starting material may be obtained as follows, using 4-mercapto-phenyl-acetic acid ethyl ester and 6-chloro-phthalide as starting materials:
a. 4-(2-carboxy-4-chloro-benzyl-thio)phenyl-acetic acid ethyl ester, produced in a manner analogous to Example 1(c): M.P. 109°–112° (from ether/pentane.
b. 4-(2-carboxy-4-chloro-benzyl-thio)phenyl-acetic acid, produced in a manner analogous to Example 1(d).

EXAMPLE 6

8-chloro-6,11-dihydro-11-oxo-dibenzo[b,e]thiepine-2-acetic acid

This compound is produced in a manner analogous to that described in Example 1, using 4-(2-carboxy-5-chloro-benzyl-thio)phenyl acetic acid as starting material. M.P. 245°–247°.

EXAMPLE 7

9-acetylamino-6,11-dihydro-11-oxo-dibenzo[b,e]thiepine-2-acetic acid

50 G of 4-(4-acetylamino-2-carboxy-benzyl-thio)-phenyl-acetic acid are stirred at 100° for 1½ hours together with 500 g of polyphosphoric acid. The resulting dark red solution is poured on 500 g of ice and the precipitated crystals are extracted with ethyl acetate. The organic phase is dried with sodium sulphate, purified with charcoal, filtered, and the solvent is removed by distillation at reduced pressure, whereby the title compound crystalizes. M.P. 210°–213°.

The starting material may be obtained as follows:
a. 4-(4-acetylamino-2-carboxy-benzyl-thio)phenyl-acetic acid ethyl ester, produced in a manner analogous to Example 1(c), using 4-mercapto-phenylacetic acid ethyl ester and 6-acetyl-amino phthalide as starting materials. M.P. 170° (from ethyl acetate/ether).
b. 4-(4-acetylamino-2-carboxy-benzyl-thio)phenylacetic acid, produced in a manner analogous to Example 1(d): M.P. 205°–207°.

EXAMPLE 8

6,11-dihydro-8-methyl-11-oxo-dibenzo[b,e]thiepine-2-acetic acid

This compound is produced in a manner analogous to that described in Example 1 or 2, using as starting material 4-(2-carboxy-5-methyl-benzyl-thio)phenyl-acetic acid [M.P. 94°, produced in a manner analogous to Example 1(d)] or 4-(2-carboxy-5-methylbenzyl-thio)phenyl-acetic acid ethyl ester [M.P. 170°–172°, produced in a manner analogous to Example 1(c) from 5-methyl-phthalide and 4-mercapto-phenyl-acetic acid ethyl ester]. M.P. of the title compound 194°–200° (from ethyl acetate).

EXAMPLE 9

6,11-dihydro-(α-methyl)-11-oxo-dibenzo[b,e]thiepine-2-acetic acid [process variant (b)]

19.5 G of 6,11-dihydro-(α-methyl)-11-oxodibenzo[b,e]thiepine-2-acetic acid ethyl ester are dissolved in 100 cc of ethanol, and 13.4 g of potassium hydroxide dissolved in 70 cc of water are added. The solution is subsequently stirred at room temperature for 15 hours. The solution is subsequently acidified with 5 N hydrochloric acid and extracted with ether. After drying over sodium sulphate and evaporating the solvent at reduced pressure, the title compound crystallizes. M.P. 138°–140°.

The starting material may be obtained as follows:
a. 6,11-dihydro-11-oxo-dibenzo[b,e]thiepine-2-acetic acid ethyl ester 40 g of 6,11-dihydro-11-oxo-dibenzo[b,e]thiepine-2-acetic acid are boiled at reflux for 45 minutes together with 400 cc of 3 N hydrochloric acid in ethanol. The reaction mixture is completely concentrated by evaporation at reduced pressure and the oily residue is divided between ethyl acetate and water; the organic phase is washed with a 10% sodium bicarbonate solution and with water. After drying over sodium sulphate and concentrating, 6,11-dihydro-11-oxo-dibenzo[b,e]thiepine-2-acetic acid ethyl ester crystallizes by the addition of ether. (M.P. 98°–100°).

b. 6,11-dihydro-(α-methyl)-11-oxo-dibenzo[b,e]thiepine-2-acetic acid ethyl ester 2.4 G of finely cut sodium are added portionwise to 300 cc of ammonia condensed at −40°, with the addition of 200 mg of iron (III) nitrate. Stirring is effected for 30 minutes at the same temperature and 300 cc of ether are subsequently allowed to flow slowly into the reaction mixture. 31.2 g of 6,11-dihydro-11-oxo-dibenzo[b,e]thiepine-2-acetic acid ethyl ester are subsequently added portionwise. After 15 minutes, the salt formation is complete. 17.0 G of methyl iodide in 100 cc of ether are added dropwise at −40°. After a further 15 minutes, the reaction is complete. The ammonia is removed by evaporation and successively replaced by 300 cc of ether. The organic phase is finally shaken with 50 g of ammonium chloride dissolved in water and is washed with water until neutral. The solution which has been purified with charcoal and dried over sodium sulphate, is concentrated at reduced pressure and pentane is added thereto, whereby 6,11-dihydro-(α-methyl)-11-oxo-dibenzo[b,e]thiepine-2-acetic acid ethyl ester crystallies. M.P. 91°–93°.

EXAMPLE 10

9-chloro-6,11-dihydro-α-methyl-11-oxo-dibenzo[b,e]thiepine-2-acetic acid

The title compound is obtained in a manner analogous to that described in Example 9, using 9-chloro-9,11-dihydro-α-methyl-11-oxo-dibenzo[b,e]thiepine-2-acetic acid ethyl ester as starting material. M.P. 128°–131° (from ether/pentane).

The starting material may be obtained as follows:
a. 9-chloro-6,11-dihydro-11-oxo-dibenzo[b,e]thiepine-2-acetic acid ethyl ester, produced in a manner analogous to Example 9(a) [M.P. 68°–71° (from acetic acid/pentane)].
b. 9-chloro-6,11-dihydro-α-methyl-11-oxo-dibenzo[b,e]thiepine-2-acetic acid ethyl ester, produced in a manner analogous to Example 9(b), oily Rf value = 0.6 (DC system: adsorbent: silica gel; eluant: ammonia-saturated ether/hexane 80:20).

EXAMPLE 11

6,11-dihydro-11-oxo-dibenzo[b,e]thiepine-2-acetic acid 6,11-dihydro-11-oxo-dibenzo[b,e]thiepine-2-acetic acid ethyl ester is hydrolyzed in a manner analogous to that described in Example 9. M.P. of the title compound 164°–165°.

The 6,11-dihydro-11-oxo-dibenzo[b,e]thiepine-2-acetic acid ethyl ester, used as starting material, may be obtained in accordance with the following methods:
a. 7.0 g of 4-(2-chloro-carbonyl-benzyl-thio)phenylacetic acid ethyl ester are heated in an oil bath of 100° together with 70 g of polyphosphoric acid, whereby a brown-red solution results with the separation of hydrochloric acid. After 30 minutes, the viscous oil is poured on a mixture of ice/water and extracted with ether. The organic phase is separated, dried with sodium sulphate, purified with charcoal, and the solvent is removed at reduced pressure and the resulting residue taken up in ether. 6,11-Dihydro-11-oxo-dibenzo[b,e]thiepine-2-acetic acid ethyl ester crystallizes from ether/pentane. M.P. 96°–97°.

b. 7.0 g of 4-(2-chloro-carbonyl-benzyl-thio)phenylacetic acid ethyl ester are dissolved in 30 cc of nitrobenzene and this solution is added dropwise, at room temperature, to a solution of 3.32 g of aluminium chloride in 50 cc of nitrobenzene. The resulting red solution is then heated in an oil bath of 100° for 3 hours. The reaction solution is subsequently poured on a mixture of ice and 10 N hydrochloric acid, is diluted with ether, and the organic phase is separated, washed with water, dried with sodium sulphate, purified with charcoal and filtered. The solvent is completely removed at reduced pressure and the oily residue is dissolved in ether, the ether phase is washed with a 10% sodium bicarbonate solution and then with water, is dried with sodium sulphate, filtered, and the solvent is removed by distillation at reduced pressure. 6,11-Dihydro-11-oxo-dibenzo[b,e]thiepine-2-acetic acid ethyl ester crystallizes from ether/pentane. M.P. 96°–97°.

The following acids may also be obtained in a manner analogous to that described in Example 11, by hydrolysis of the corresponding ethyl esters:

EXAMPLE 12

9-chloro-6,11-dihydro-11-oxo-dibenzo[b,e]thiepine-2-acetic acid

M.P. 187°–189° (from ethyl acetate/pentane).

EXAMPLE 13

8-chloro-6,11-dihydro-11-oxo-dibenzo[b,e]thiepine-2-acetic acid

M.P. 245°–247°.

EXAMPLE 14

9-acetylamino-6,11-dihydro-11-oxo-dibenzo[b,e]thiepine-2-acetic acid

M.P. 210°–213°.

EXAMPLE 15

9-amino-6,11-dihydro-11-oxo-dibenzo[b,e]thiepine-2-acetic acid

M.P. of the hydrochloride form 240° (decomposition, from acetone).

EXAMPLE 16

6,11-dihydro-9-hydroxy-11-oxo-dibenzo[b,e]thiepine-2-acetic acid

M.P. 192°–195°.

EXAMPLE 17

6,11-dihydro-8-methyl-11-oxo-dibenzo[b,e]thiepine-2-acetic acid

M.P. 194°–200°.

EXAMPLE 18

6,11-dihydro-9-methoxy-11-oxo-dibenzo[b,e]thiepine-2-acetic acid 1.0 G of 6,11-dihydro-9-methoxy-11-oxodibenzo[b,e]thiepine-2-acetic acid methyl ester is dissolved in 10 cc of methanol, and 0.4 g of potassium hydroxide, dissolved in 2 cc of water, are added. The solution is stirred at room temperature for 16 hours. The methanol is then removed by distillation at reduced pressure, the residue is dissolved in water and extracted with ether. The alkaline, aqueous phase is then acidified with 2 N hydrochloric acid and extracted with ether. The ether extract is dried with sodium sulphate, purified with charcoal, filtered and concentrated at reduced pressure, whereby the title compound crystallizes. M.P. 155°–157°.

The starting material may, for example, be produced as follows:

a. Example of process variant (c)

6.7 G of 9-acetamido-6,11-dihydro-11-oxo-dibenzo[b,e]thiepine-2-acetic acid are boiled at 120° for 3 hours, in 134 cc of 10 N hydrochloric acid. Cooling is then effected, 200 cc of acetone are added, and the precipitated 9-amino-6,11-dihydro-11-oxo-dibenzo[b,e]thiepine-2-acetic acid hydrochloride is filtered off. M.P. 240° (decomp.)

b. Example of process variant (d)

1.0 G of 9-amino-6,11-dihydro-11-oxo-dibenzo[b,e]thiepine-2-acetic acid hydrochloride is mixed with 10 cc of water, 10 cc of glacial acetic acid and 0.5 cc of sulphuric acid (98%). A solution of 0.25 g of sodium nitrite in 2 cc of water is added dropwise at 0°–5° to the resulting solution. After the dropwise addition is complete, a further 4 cc of 89% sulphuric acid are added. The resulting diazo compound is allowed to flow in a thin stream into 50 cc of 50% sulphuric acid having a temperature of 125°. Heating is effected for a further 15 minutes while stirring vigorously. The reaction mixture is then cooled to room temperature and poured on 250 cc of ice water. The resulting yellow precipitate is extracted with ether, the organic phase is washed with water, dried with sodium sulphate, filtered and concentrated by evaporation. 6,11-Dihydro-9-hydroxy-11-oxo-dibenzo[b,e]thiepine-2-acetic acid crystallizes from ether/pentane. M.P. 192°–195°.

c. 1.0 G of 6,11-dihydro-9-hydroxy-11-oxo-dibenzo[b,e]thiepine-2-acetic acid is dissolved in 10 cc of methanol, 1 cc of water is added and cooling is effected in an ice bath. 60 CC of a 2% ethereal diazomethane solution are allowed to flow into the solution while stirring. The yellow solution is stirred for a further 2 hours at 0°–5° and for 1 hour at room temperature. The solvent is subsequently removed by distillation at reduced pressure, the residue is again taken up in ether and washed with a 1 N caustic soda solution. After washing with water, the organic phase is dried with sodium sulphate, filtered and completely concentrated by evaporation at reduced pressure, whereby 6,11-dihydro-9-methoxy-11-oxo-dibenzo[b,e]thiepine-2-acetic acid methyl ester is obtained as brown-yellow oil which is purified by chromatography. Thin layer chromatogram: $R_f$ value 0.4 (adsorbent: silica gel G with luminous substance, eluant: aqueous ammonia-saturated ether/hexane 80:20).

EXAMPLE 19

8-Chloro-6,11-dihydro-α-methyl-11-oxodibenzo[b,e]thiepine-2-acetic acid

In analogous manner to that described in Example 9, 8-chloro-6,11-dihydro-α-methyl-11-oxo-dibenzo[b,e]thiepine-2-acetic acid is made. M.P. 137°–138°.

The compounds of formula I are useful as anti-phlogistic agents for the inhibition of oedemas, as indicated in standard tests, for example by an inhibition of oedema formation in the carrageen paw oedema test in rats on p.o. administration of from 5 to 100 mg/kg animal body weight of the compounds, and in the subchronic granuloma cyst test on administration of from 20 to 100 mg/kg animal body weight of the compounds.

For this use the dosage will, of course, vary depending on the compound employed, mode of administration and treatment desired. However, in general, satisfactory results are obtained when administered at a daily dosage of from about 1 mg to about 100 mg per kg animal body weight, conveniently given in divided doses two to four times a day or in sustained release form. For the larger mammals, the total daily dosage is in the range from about 100 to about 1000 mg, and dosage forms suitable for oral administration comprise from about 25 mg to about 500 mg of the compounds admixed with a solid or liquid pharmaceutical carrier or diluent.

The compounds of formula I are furthermore useful as anti-arthritic agents, as indicated in standard tests, for example, by an inhibition of swellings in the Freund adjuvant arithritis latent period test in rats on p.o. administration of from 30 to 100 mg/kg animal body weight of the compounds.

For this use the dosage will, of course, vary depending on the compound employed, mode of administration and treatment desired. However, in general, satisfactory results are obtained when administered at a daily dosage of from about 1 mg to about 100 mg per kg animal body weight, conveniently given in divided doses two to four times a day or in sustained release form. For the larger mammals, the total daily dosage is in the range from about 100 to about 1000 mg, and dosage forms suitable for oral administration comprise from about 25 mg to about 500 mg of the compounds admixed with a solid or liquid pharmaceutical carrier or diluent.

The compounds of formula I may be administered in pharmaceutically acceptable salt form. Such salt forms exhibit the same order of activity as the free acid forms. Representative salt forms include alkali metal salts such as the sodium or potassium salt, alkaline earth metal salts such as the calcium salt and also include organic salts such as the ammonium salt and amine salts such as the dimethylamine, diethylamine, trimethylamine and benzylamine salts. Such compositions conveniently contain more than 1% by weight of the compound of formula I and may be prepared by conventional techniques to be in conventinal forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastro-intestinal tract and thereby provide sustained action over a long period.

The Example 1 and 9 compounds exhibit particularly interesting activity.

In a group of compounds $R_1$ is hydrogen, halogen, alkyl or alkoxy. In one sub-group $R_2$ is alkyl. In another sub-group $R_2$ is hydrogen.

In another group of compounds $R_1$ is in the 9-position. Preferably $R_1$ is hydrogen, halogen, alkyl or alkoxy. In a sub-group $R_2$ is methyl.

I claim:

1. A compound of the formula:

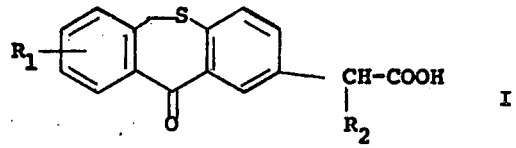

wherein
$R_1$ is hydroxyl, lower alkoxy, amino or acetamino, and
$R_2$ is hydrogen or lower alkyl,
or a pharmaceutically acceptable salt thereof.

2. A compound of claim 1 wherein $R_1$ is amino.

3. The compound of claim 1 which is 9-acetylamino-6,11-dihydro-11-oxo-dibenzo[b,e]thiepine-2-acetic acid.

4. The compound of claim 1 which is 9-amino-6,11-dihydro-11-oxo-dibenzo[b,e]thiepine-2-acetic acid.

5. The compound of claim 1 which is 6,11-dihydro-9-hydroxy-11-oxo-dibenzo[b,e]thiepine-2-acetic acid.

6. The compound of claim 1 which is 6,11-dihydro-9-methoxy-11-oxo-dibenzo[b,e]thiepine-2-acetic acid.

* * * * *